United States Patent [19]

Devisetty et al.

[11] 4,224,049

[45] Sep. 23, 1980

[54] COMPATIBILITY AGENTS AND METHOD OF USE

[75] Inventors: Bala N. Devisetty; James R. Hanson, both of Madison, Wis.

[73] Assignee: Hopkins Agricultural Chemical Co., Madison, Wis.

[21] Appl. No.: 956,657

[22] Filed: Nov. 1, 1978

[51] Int. Cl.$^2$ .......................... A01N 9/02; A01N 9/36
[52] U.S. Cl. ................................... 71/86; 71/DIG. 1; 71/3; 71/93; 71/122; 252/351; 252/358
[58] Field of Search ................. 71/3, 86, 122, DIG. 1, 71/93

[56] References Cited

U.S. PATENT DOCUMENTS

| | | | |
|---|---|---|---|
| 2,770,538 | 11/1956 | Vierling | 71/3 |
| 2,829,151 | 4/1958 | Britton et al. | 71/86 |

FOREIGN PATENT DOCUMENTS

| | | |
|---|---|---|
| 2251072 | 9/1971 | Fed. Rep. of Germany. |
| 966820 | 8/1964 | United Kingdom. |

OTHER PUBLICATIONS

McCutcheon, "Detergents & Emulsifiers" Int. Ed. (1976), p. 3.
Becher, "Emulsions, Theory & Practice" (1965) pp. 11, 220.

*Primary Examiner*—Donald G. Daus
*Assistant Examiner*—David E. Wheeler

[57] ABSTRACT

Compatibility agents were developed for improving the compatibility and stability of mixtures of liquid fertilizers and liquid or wettable powdered pesticides. These compatibility agents contain water, a low alkanol and an alkylaryl polyoxyethylene glycol phosphate ester. The compatibility agent is used at a preferred concentration range of 0.1 to 0.4% of the fertilizer solution. The preferred compatibility agent not only improves the compatibility of liquid fertilizer-pesticide mixtures, but also results in uniform and stable mixtures ensuring accurate pesticide applications. The preferred compatibility agent is a mixture containing about 16% water, about 20% methanol and about 64% of an octylphenol polyoxyethylene glycol phosphate ester.

17 Claims, No Drawings

COMPATIBILITY AGENTS AND METHOD OF USE

SUMMARY OF THE INVENTION

The present invention relates generally to the field of agricultural chemistry, and, more specifically, to compatibility agents for improving the stability and uniformity of mixtures of liquid fertilizer and pesticides.

The advantages of simultaneous application of liquid fertilizer and pesticide(s) are twofold: (1) a single application saves time as well as labor, and (2) reduces soil compaction by eliminating a field operation. Unfortunately, most pesticides are either noncompatible or form unstable mixtures in liquid fertilizers. This incompatibility can result in the formation of substances resembling thick creams or oil scum which settle on the bottom of the tank, float on the top or coat the inside. Spraying of such incompatible mix results in uneven distribution, poor performance, crop injury and building up of soil and crop residues.

Previous attempts to improve the uniformity and stability of such pesticide and liquid fertilizer mixtures by incorporating into the mixtures known emulsifying and suspending agents, as compatibility agents, have been relatively unsuccessful. Therefore, a need still exists for compatibility agents which improve the stability and uniformity of normally incompatible mixtures of pesticides and liquid fertilizers so that both the pesticides and fertilizer can be simultaneously applied to crops.

We have discovered compatibility agents which satisfy that need and which make possible the preparation of more stable and uniform suspensions and emulsions of pesticides and liquid fertilizers. The compatibility agents we have found to be useful are aqueous-lower alkanol solutions containing an alkylaryl polyoxethylene glycol phosphate esters.

DETAILED DESCRIPTION OF THE INVENTION

The compatibility agents of the present invention are aqueous-lower alkanol solutions containing an alkylaryl polyoxyethylene glycol phosphate ester of the following formula:

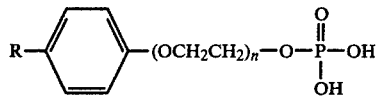

in which R is 6 to 12 carbons and n is 4 to 10.

The compatibility agent preferably contains from 10 to 30% water, 10 to 40% of a lower alkanol of 1 to 6 carbon atoms such as methanol, isopropyl alcohol, n-propyl alcohol, isobutyl alcohol, n-butyl alcohol, sec.-butyl alcohol, tert. butyl alcohol, ethylene glycol, diethylene glycol, and triethylene glycol, and 30 to 80% of the alkylaryl polyoxyethylene glycol phosphate ester. If desired, coloring agents, defoaming agents, buffering agents, or other ingredients which do not interfere with the functions of the compatibility agent may be incorporated.

The phosphate ester which is preferred for use in the compatibility agent is octylphenol polyoxyethylene glycol phosphate ester. It may be represented by the following formula:

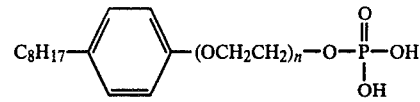

in which n is 5 to 8. Like the other esters which can be used, it is an anionic surface active agent. Its major use in the past has been as a solubilizer and surfactant in detergent formulas. The preferred ester is commercially available from the Rohm and Haas Company under the special trademark HA-88.

The preferred compatibility agent contains about 20% methanol, about 16% water and about 64% the octylphenol polyoxyethylene glycol phosphate ester.

The preferred compatibility agent is prepared by blending the methanol to a viscous solution containing the phosphate ester and the water. The resulting solution having a viscosity of 200 cps and specific gravity of 1.1 is stable at temperatures ranging from $-21°$ C. to $+50°$ C., and is easily and uniformly mixed with liquid fertilizers and water.

In the preferred method of use, the compatibility agent is added to the liquid fertilizer in an amount which ranges from about 0.1% to about 0.4% by volume of the fertilizer solution and the pesticide is then added to the resulting mixture. The suspensions and emulsions thus obtained are more uniform in composition and more stable than those prepared without the compatibility agent. The stability and uniformity which insures a more accurate application of the pesticide depends to some extent upon the liquid fertilizer and pesticide employed, as well as, the concentration of the compatibility agent and the manner in which the various components are mixed.

The liquid fertilizers referred to herein include liquid nitrogen fertilizer (e.g., 28% and 32% solutions) and the liquid mixed fertilizers which in addition to nitrogen contain various amounts of other ingredients such as phosphate and potash (e.g., 4-10-10, 6-18-6, 9-18-9, 7-23-5).

The pesticides which normally experience compatibility problems with liquid fertilizers include such commonly used herbicides; Aatrex 4L, Aatrex 80W, Banvel 4EC, Bladex 4L, Bladex 80W, Dow Formula 44, DMA-4, Eptam 7E, Lasso 4EC, Lasso 4EC(LF), Lexone 50W, Lexone 4L, Prowl 4EC, Sencor 4L, Sencor 50W, Sutan+6.7 E, Tolban 4EC, Treflan 4EC, Trimec, etc. Commonly used insecticides such as Diazinon 4EC, Dyfonate 4E, Furadan 4F, and Lorsban 4E, and common fungicides such as Arasan 42S, Bravo 6F, and Dithane M-45 also present serious compatibility problems when using with liquid fertilizers. In all of these cases, we have found that the compatibility agent of the present invention will greatly improve the uniformity and stability of emulsions formed in various liquid fertilizers. The compatibility problems associated with pesticide(s) in water can also be overcome by the present invention. (Examples: Bladex 80W+Lasso 4EC and Arasan 42S+Bravo 6F).

The following are guidelines for the use rates of the compatibility agents:

| | |
|---|---|
| Liquid Nitrogen Fertilizer (28-0-0, 32-0-0) & Pesticides: | 1-3 pints/100 gallons of fertilizer |
| Liquid Mixed Fertilizers | 2-3 pints/100 |

| (4-10-10, 10-10-10, 12-6-6, 15-5-5, 6-18-6, 3-18-18, 9-18-9, 7-23-5, 10-34-0) & Pesticides: | gallons of fertilizers |
|---|---|
| Multiple Pesticide and Fertilizer Combinations: | 2-3 pints/100 gallons of fertilizer |

Compatibility Test: A simple test using small proportional quantities of the components can provide growers and custom applicators with the compatibility potential of their chemicals. The following reasons will better explain why a test of physical compatibility is required.

(a) Liquid fertilizers differ in density, viscosity, salt concentration, and nutrient analysis. Because there is an almost endless number of fertilizer solutions, varying in grade and analysis, solutions may react differently in combination with the added pesticides.

(b) Pesticides vary in formulation and application rate.

(c) Improper mixing can be costly and time consuming when applying pesticides. This can result in inaccurate pesticide applications, poor performance, increased soil and crop residues and dissatisfaction to the grower.

(d) To determine appropriate rate and mixing method while using the compatibility agents.

The suggested test procedure comprises:

1. Adding 1 pint of liquid fertilizer to each of 2 clean jars, marked 'with' and 'without.'

2. Adding ¼ teaspoon or 1.2 ml. of compatibility agent to the jar marked 'with' (¼ teaspoon is the equivalent of 2 pints/100 gallons of liquid fertilizer).

3. Adding the appropriate amount of pesticide (see Tables 1 and 2) to each jar. If more than one is used, add them separately with the wettable powders first in the form of slurry, flowables second, and emulsifiable concentrates last.

4. Shaking the jars thoroughly to mix and then allowing the jars to stand 15-30 minutes.

5. Comparing the mixtures in the jars and noting the uniformity of the dispersion of the mixtures without the formation of large flakes, sludge, gels, or other precipitates.

If the mixture in the jar marked 'with' is not sufficiently stable and uniform, the test is repeated using ⅜ teaspoon or 1.8 ml. of the compatibility agent (⅜ teaspoon is the equivalent of 3 pints/100 gallons of fertilizer.) If the mixture is still not sufficiently stable and uniform, a premix of the compatibility agent and the pesticide(s) is prepared and added to the liquid fertilizer with mixing to obtain optimum results.

Table 1

Guideline of Pesticide Rates for Compatibility Testing

| Gallons of Liquid Fertilizer To Be Applied/Acre | Teaspoons* of Liquid Pesticide to Be Added Per Pint of Liquid Fertilizer | | |
|---|---|---|---|
| | 1 QT/A | 2 QT/A | 4 QT/A |
| 10 | 2.4 | 4.8 | 9.6 |
| 20 | 1.2 | 2.4 | 4.8 |
| 40 | 0.6 | 1.2 | 2.4 |
| 60 | 0.4 | 0.8 | 1.6 |
| 80 | 0.3 | 0.6 | 1.2 |
| 100 | 0.2 | 0.5 | 1.0 |

*1 teaspoon = 4.93 ml.

Table 2

Guideline of Wettable Powder Pesticide Rates for Compatibility Testing.

| Gallons of Liquid Fertilizer To Be Applied/Acre | Teaspoons* of Wettable Powder Pesticide To Be Added/Pint of Liquid Fertilizer | | |
|---|---|---|---|
| | 1 LB/A | 2 LB/A | 4 LB/A |
| 10 | 3.5 | 7.1 | 14.2 |
| 20 | 1.8 | 3.5 | 7.1 |
| 40 | 0.9 | 1.8 | 3.5 |
| 60 | 0.6 | 1.2 | 2.4 |
| 80 | 0.4 | 0.9 | 1.8 |
| 100 | 0.3 | 0.7 | 1.4 |

*Teaspoon = 1.6g. Based on 80% WP Pesticide Formulations

When evaluating compatibility to determine the appropriate use rate, a minimum stability period of 30, and preferably 60, minutes with no agitation is considered the acceptability criterion. Separation of marginally compatible blends can occur in spray hoses during intermittent operation or during normal continuous operation. Such variations in material distribution can reduce effectiveness of applications, even though not sufficient to cause nozzle plugging. A longer stability period should be considered when intermittent application or transportation between fields will occur.

There are several alternative methods for mixing the compatibility agent with the fertilizer and pesticide. They are the following:

Method I

1. Add the required amount of liquid fertilizer in the spray tank.
2. Add the required amount of compatibility agent to the liquid fertilizer and mix thoroughly.
3. Add the required amount of pesticide and mix the contents thoroughly.

Method II

1. Add the required amount of liquid fertilizer in the spray tank.
2. Add the required amount of compatibility agent to the liquid fertilizer.
3. Add the required amount of pesticide and then mix the contents thoroughly.

Method III

1. Add the required amount of liquid fertilizer in the spray tank.
2. Prepare a premix of required quantity of compatibility agent and pesticide. Add to the liquid fertilizer and mix contents thoroughly.

Methods I and II are applicable for most situations. Method III is suggested where compatibility problems arise where it is desired to apply two or more pesticides through a single source of liquid fertilizer. Method III is also recommended for mixtures involving high phosphatic grade liquid fertilizers (6-18-6, 9-18-9, 3-18-18, 7-23-5, 10-34-0) and flowable pesticide formulations. (e.g., Furadan 4F, Aatrex 4L, Bladex 4L, Bravo 6F.)

It should be noted that some form of agitation in the spray tank during application may be required for certain liquid fertilizer-pesticide combinations. In addition, if the spray mixture has been allowed to stand, it is desirable to agitate the tank mix before application.

The practice of the invention is further illustrated by the following Examples:

EXAMPLES

General Test Procedure

The liquid fertilizer (50 ml.) was added to an emulsion tube. The required amounts of pesticide and the compatibility agent were added to the fertilizer and the emulsion tubes were given 5-10 full immersions to obtain a uniform mix. The contents of the emulsion tube were checked visually for dispersion, column appearance, precipitation, layer separation, etc. at different time intervals, and the results observed compared to those observed in control tubes not containing the compatibility agent. The specific details of the various tests performed are summarized below.

EXAMPLE A

The above described general test procedure was employed to evaluate the compatibility of the herbicides Lasso 4EC (use rate 2 quarts per acre), Bladex 4L (use rate $2\frac{1}{2}$ quarts per acre), Ciba-Geigy Atrazine 4L (use rate $2\frac{1}{2}$ quarts per acre), Lasso 4EC and Bladex 4L (use rate 2 and $2\frac{1}{2}$ quarts per acre), and Lasso 4EC and Atrazine 4L (use rate 2 and $2\frac{1}{2}$ quarts per acre). The compatibility agent employed was a mixture of 64% of an octophenol polyoxyethylene glycolphosphate ester, (molecular weight about 490), about 16% water and about 20% methanol. The compatibility agent was added in an amount equivalent to 2 pints/100 gallons of 15-5-5 grade liquid mixed fertilizer. Controls containing no compatibility agent were also prepared.

In the controls the herbicides started separating from the fertilizer solution in less than 5 minutes. In the emulsion tubes containing the compatibility agent, excellent emulsions were formed. Observations were made at the end of one hour, and it was noted that there was a complete separation of the herbicide from the fertilizers in the controls. No such separation was noticed in the emulsion tubes containing compatibility agents. Furthermore, there was no evidence of separation in the mixtures containing the compatibility agent at 19 hours.

EXAMPLE B

The procedure of Example A was repeated using a liquid fertilizer grade 6-18-6; Lasso (2 quarts per acre), Drexel brand Atrazine 4L ($2\frac{1}{2}$ quarts per acre), and Lasso 4EC plus Drexel brand Atrazine 4L (2 plus $2\frac{1}{2}$ quarts per acre). The same compatibility agent was used, but at a rate of 2 and 3 pints per 100 gallons for the mixtures containing individual pesticides and at a rate of 2, 3 and 4 pints per 100 gallons for the mixtures containing combinations of pesticides.

In the controls, the Lasso initially mixed well with the fertilizer, but then separated out in less than 3 minutes. In the samples with the compatibility agent, there was no evidence of such separation. The Drexel brand Atrazine did not mix well in the fertilizer and even the Drexel Atrazine mixture containing the compatibility agent needed agitation to obtain proper mixing. The Atrazine and Lasso control mixtures formed a good suspension; however, in the presence of the compatibility agent the suspension was more uniform.

At 30 and 60 minutes the mixture containing Lasso with the compatibility agent appeared to be stable; however, in the control without the compatibility agent there was a complete separation of the Lasso. There was no evidence of separation of the Atrazine from the fertilizer with or without the compatibility agent. However, the mixture containing the compatibility agent was more uniform. The use of the compatibility agent at 3 pints per 100 gallons resulted in the formation of finer suspension than that obtained when 2 pints per 100 gallons was employed.

In the mixture containing the Lasso and Drexel brand Atrazine combination, Lasso separation was noted in the controls. No Lasso separation was noted in the mixtures containing two or three pints of the compatibility agent per 100 gallons of fertilizer. The suspensions obtained at the 3 pints per 100 gallon rate of use were finer than those obtained at lower rates of use.

At 18 hours, the Lasso fertilizer mixture containing the compatibility agent was still stable. The Atrazine fertilizer mixtures with or without the compatibility agent also still appeared to be stable. The controls containing the mixtures of Lasso and Atrazine had separated, whereas, the mixtures containing the combination of the pesticides and the compatibility agent were stable.

The test results indicate that with this grade liquid fertilizer, the compatibility agent at 3 pints per 100 gallons performed better than that at 2 pints per 100 gallons. Both the stability and uniformity of the mixtures formed at the 3-pint rate was slightly superior to that formed at the 2-pint rate. However, the results also indicated that where longer stability is not desired, the compatibility agent could be used at the rate of 2 pints per 100 gallons of fertilizer.

EXAMPLE C

The procedure of Example A was repeated using the liquid fertilizer grade 6-18-6 with Atrazine (Ciba-Geigy) at the use rate of $2\frac{1}{2}$ quarts and Lasso plus Atrazine (Ciba-Geigy) at the use rate of 2 and $2\frac{1}{2}$ quarts, respectively. The compatibility agent was used at a rate of 1, 2 and 4 pints per 100 gallons of fertilizer.

Initial observations indicated that the Atrazine (Ciba-Geigy brand) did not mix well with the fertilizer; even with the compatibility agent present agitation was necessary.

At one hour the Atrazine-fertilizer mixture seemed to be stable even in the absence of compatibility agent, but there were significantly less floating particles in the mixtures containing 2 pints of the compatibility agent or more. In the Lasso-Atrazine combination containing controls, all the Lasso and part of the Atrazine separated from the fertilizer solution after one hour. In contrast, the mixture containing 2 pints compatibility agent per 100 gallons of the fertilizer was stable.

EXAMPLE D

The procedure of Example A was repeated using the liquid fertilizer 28-0-0 (30 gallons/acre); the herbicides employed were Prowl 4EC (2 quarts/acre) and Sencor 50W (1.5 pounds/acre). The compatibility agent was employed at the rate of one and two pints/100 gallons of fertilizer. Mixing Method II was used for mixing the herbicides and compatibility agent. The herbicides in the fertilizer mixture containing no compatibility agent separated in less than 15 minutes. The compatibility agent helped in obtaining compatible and stable mixtures for 24 hours or more.

EXAMPLE E

The compatibility of Treflan 4EC (1 quart/acre) plus Sencor 4L (½ quart/acre) was tested in the liquid fertilizer 4-10-10 (30 gallons/acre). The preferred compatibility agent was employed at 3 pints/100 gallons. Mixing Method III was employed. In the control, the herbicides separated from the fertilizer in less than 5 minutes. The mixture containing the compatibility agent was stable for 24 hours or more.

EXAMPLE F

The procedure of Example A was repeated using the liquid fertilizer 12-6-6. The following herbicides were tested at the rates indicated; Lasso 4EC (2 quarts per acre), Bladex 4L (2½ quarts per acre), Ciba-Geigy brand Atrazine 4L (2½ quarts per acre), Hopkins brand Atrazine 80W (2 pounds per acre), Lasso A4EC plus Bladex 4L (2 plus 2½ quarts per acre), Lasso plus Ciba-Geigy brand Atrazine 4L (2 plus 2½ quarts per acre) and Lasso plus Hopkins brand Atrazine 80W (2 quarts plus 2 pounds). The compatibility agent was used at a rate of 2 pints per 100 gallons of fertilizer. The initial observations indicated that without the use of the compatibility agent, none of the herbicides, alone or in combination, were compatible with this grade fertilizer. However, with the compatibility agent present the compatibility of all the mixtures was excellent.

At one hour, the herbicide and fertilizer mixtures that included the compatibility agent were stable. However, in all the controls there was a complete separation of the herbicides from the fertilizers. Later observations verified that even at 17 hours the herbicide-fertilizer mixtures containing the compatibility agent were still stable.

EXAMPLE G

The compatibility of the insecticide, Dyfonate 4E (1 to 2 quarts per acre) with the liquid fertilizers; 28-0-0, 9-18-9, 12-6-6, 15-5-5 and 6-18-6 was evaluated. The same compatibility agent and procedure was used as in Example A. The compatibility agent was used at the rate of 1 to 3 and 4 pints per 100 gallons. Controls were also prepared.

After one hour the following results were observed:

Liquid fertilizer grade 28-0-0: The mixtures without the compatibility agent separated. Those with the compatibility agents were compatible and stable emulsions.

Liquid fertilizer grade 9-18-9: The mixtures containing Dyfonate without the compatibility agent separated. The mixture containing the compatibility agent was uniform and stable.

Liquid fertilizer grade 6-18-6: The control separated out; the mixture containing the compatibility agent was uniform and stable.

Liquid fertilizer grade 12-6-6: Both the control and the mixture with the compatibility agent were stable.

Liquid fertilizer grade 15-5-5: The control showed some separation while the mixture with the compatibility agent was stable.

Observations at 17 hours indicated that the emulsions were still stable, although some separation appeared to be occurring.

EXAMPLE H

The compatibility of the herbicide Sutan+6.7E at the rate of 2 quarts per acre was evaluated in combination with the liquid fertilizer grades 28-0-0, 9-18-9, 12-6-6, 15-5-5 and 6-18-6.

The compatibility agent of Example A was added at the rate of 2 pints per 100 gallons. The compatibility agent was added to the fertilizer; the herbicide was added and the three ingredients mixed.

At one hour, the following results were noted:

| Liquid Fertilizer Grade | Observations |
| --- | --- |
| 28-0-0 | Compatible and stable with compatibility agent. Control separated. |
| 9-18-9 | Compatible and stable with compatibility agent. Control separated. |
| 12-6-6 | Compatible and stable with compatibility agent. Control complete separation in less than 30 minutes. |
| 15-5-5 | Compatible and stable with compatibility agent. Control complete separation of herbicides in less than 30 minutes |
| 6-18-6 | Compatible and stable with compatibility agent. Control complete separation of herbicides in less than 30 minutes. |

At 7 hours, the following results were noted:

| | |
| --- | --- |
| 28-0-0 | With compatibility agent, some separation as creamy layer. Control complete separation. |
| 12-6-6 | With compatibility agent, compatible and stable. Control complete separation. |
| 9-18-9 | The mixture containing the compatibility agent was stable. Complete separation of the herbicide occurred in the control mixture. |
| 15-5-5 | The mixture containing the compatibility agent was stable. Sutan completely separated in the control treatment. |
| 6-18-6 | Compatible and stable emulsion with the compatibility agent. Complete separation of the herbicide in the control treatment. |

EXAMPLE I

The compatibility of Eptam EC (2 quarts per acre) was evaluated in 4-10-10 liquid fertilizer in the absence and presence of the preferred compability agent (2 pints per acre). Mixing Method III was used for adding the herbicide and the compatibility agent to the fertilizer solution. The herbicide in the control treatment separated in less than 10 minutes, whereas its emulsion in the fertilizer solution containing the preferred compatibility agent was stable for 24 hours or more.

EXAMPLE J

The compatibility of Prowl 4EC (2 quarts per acre) was studied in 28% nitrogen solution (30 gallons per acre). Several compatibility agents at 3 pints per 100 gallons fertilizer were examined for this purpose. The required quantity of herbicide and the compatibility agent were added to the fertilizer and the contents were thoroughly mixed and allowed to stand. Observations on emulsion stability of the mixtures were taken at various time intervals. The compatibility agents used in this study are listed below:

J-1: The preferred compatibility agent containing 20% methanol, 16% water, and 64% of octylphenol polyoxyethylene glycol phosphate ester.

J-2: The compatibility agent containing 20% diethylene glycol, 16% water and 64% of octylphenol polyoxyethylene glycol phosphate ester.

J-3: The compatibility agent containing 20% triethylene glycol, 16% water, and 64% of the octylphenol polyoxyethylene glycol phosphate ester.

J-4: The compatibility agent containing 20% ethylene glycol, 16% water, and 64% of the octylphenol polyoxyethylene glycol phosphate ester.

J-5: The compatibility agent containing 20% propylene glycol, 16% water, and 64% of the octylphenol polyoxyethylene glycol phosphate ester.

J-6: The compatibility agent containing 20% isopropyl alcohol, 16% water, and 64% of the octylphenol polyoxyethylene glycol phosphate ester.

J-7: The compatibility agent containing 20% n-propyl alcohol, 16% water, and 64% of the octylphenol polyoxyethylene glycol phosphate ester.

J-8: The compatibility agent containing 20% n-butyl alcohol, 16% water, and 64% of the octylphenol polyoxyethylene glycol phosphate ester.

J-9: The compatibility agent containing 20% isobutyl alcohol, 16% water, and 64% of the octylphenol polyoxyethylene glycol phosphate ester.

J-10: The compatibility agent containing 18% propylene glycol, 2% methanol, 16% water, and 64% octylphenol polyethylene glycol phosphate ester.

J-11: The compatibility agent containing 10% propylene glycol, 5% methanol, 5% diethanolamine, 16% water, and 64% octylphenol polyoxyethylene glycol phosphate ester.

J-12: The compatibility agent containing 10% propylene glycol, 5% methanol, 5% tri-ethanolamine, 16% water, and 64% octylphenol polyoxyethylene glycol phosphate ester.

J-13: The compatibility agent containing 31% water, 5% diethanolamine, and 64% octylphenol polyoxyethylene glycol phosphate ester.

J-14: The compatibility agent containing 26% water, 5% methanol, 5% diethanolamine, and 64% octylphenol polyoxyethylene glycol phosphate ester.

J-15: The compatibility agent containing 15% methanol, 5% diethanolamine, 16% water, and 64% octylphenol polyoxyethylene glycol phosphate ester.

J-16: The compatibility agent containing 21% water, 10% methanol, 5% diethanolamine, and 64% octylphenol polyoxyethylene glycol phosphate ester.

The herbicide in the mixture not receiving any of the above compatibility agents separated from the fertilizer in less than 15 minutes.

Table 3

| Sr. No. | Common Name | Trade Name |
|---|---|---|
| | Common and trade names of pesticides used in the development work of the present invention: | |
| 1 | Atrazine | Aatrex, Atrazine |
| 2 | Cyanazine | Bladex |
| 3 | Dicamba | Banvel |
| 4 | 2,4-D | DMA-4, Dow Formula 44 |

Table 3-continued

| Sr. No. | Common Name | Trade Name |
|---|---|---|
| | Common and trade names of pesticides used in the development work of the present invention: | |
| 5 | EPTC | Eptam |
| 6 | Alachlor | Lasso |
| 7 | Metribuzin | Lexone, Sencor |
| 8 | Butylate | Sutan |
| 9 | Pendimethalin | Prowl |
| 10 | Profluralin | Tolban |
| 11 | Trifluralin | Treflan |
| 12 | Dimethylamine salts of 2,4-D MCPP, and Dicamba | Trimec |
| 13 | Diazinon | Diazinon |
| 14 | Fonofos | Dyfonate |
| 15 | Carbofuran | Furadan |
| 16 | Chlorpyrifos | Lorsban |
| 17 | Thiram | Arasan |
| 18 | Chlorothalonil | Bravo |
| 19 | Mancozeb | Dithane M-45 |

All the above listed 16 compatibility agents helped obtain a uniform and stable emulsion of Prowl in the nitrogen fertilizer solution. The mixtures remained stable for 24 hours or more.

In addition to the foregoing, field tests of liquid fertilizer-pesticide mixtures to which the compabitility agent had been added were performed. The tests demonstrated that such mixtures resulted in a more accurate application of the pesticide.

Although experience indicates that the compatibility agent is particularly useful in those situations where it is desired to apply two diffferent pesticides simultaneously in a single source of liquid fertilizer, the compatibility agent can be advantageously used whenever it is desired to improve the uniformity or stability of a liquid fertilizer and pesticide mixture.

We claim:

1. A compatibility agent for improving the uniformity and stability of liquid fertilizer-pesticide mixtures so that the pesticide can be accurately applied to a crop or soil in a predetermined amount by simultaneously applying the pesticide and liquid fertilizer to the crop or soil, which compatibility agent which consists essentially of water, a member selected from a lower alkanol of 1 to 6 carbon atoms, ethanolamine, diethanolamine and triethanolamine and a polyoxyethylene glycol phosphate ester of the formula:

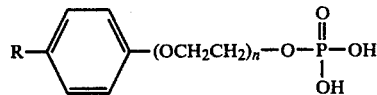

in which R is an alkyl of 6 to 12 carbon atoms, and n is 4 to 8.

2. A compatibility agent of claim 1 in which the ester is octylphenol polyoxyethylene glycol phosphate ester.

3. A compatibility agent of claim 1 in which the lower alkanol is methanol.

4. The compatibility agent of claim 1 which consists of about 64% of octylphenol polyoxyethylene glycol phosphate ester, about 16% water and about 20% methanol.

5. A compatibility agent of claim 1 in which the lower alkanol is propylene glycol.

6. A compatibility agent of claim 1 in which the lower alkanol is ethylene glycol.

7. A compatibility agent of claim 1 in which the lower alkanol is diethylene glycol.

8. A compatibility agent of claim 1 in which the lower alkanol is triethylene glycol.

9. A compatibility agent of claim 1 in which the lower alkanol is isopropyl alcohol.

10. A compatibility agent of claim 1 in which the lower alkanol is n-propyl alcohol.

11. A compatibility agent of claim 1 in which the lower alkanol is n-butyl alcohol.

12. A compatibility agent of claim 1 in which the lower alkanol is isobutyl alcohol.

13. A compatibility agent of claim 1 in which the lower alkanol is sec. butyl alcohol.

14. A compatibility agent of claim 1 in which the lower alkanol is tert. butyl alcohol.

15. A compatibility agent of claim 1 which contains a mixture of lower alkanols.

16. The method of improving the uniformity and stability of mixtures of a pesticide and a liquid fertilizer which otherwise have inadequate stability and uniformity to permit the simultaneous application of the fertilizer and pesticide at predetermined rates, which method comprises adding to the mixture of pesticide and fertilizer prior to application an effective amount of the compatibility agent of claim 1.

17. The method of simultaneously and accurately applying a predetermined amount of a pesticide and a liquid fertilizer to a crop or soil, which method comprises forming a uniform and stable mixture of the pesticide and fertilizer by incorporating therein an effective amount of a compatibility agent of claim 1 and then applying the mixture to the crop or soil before any separation of the pesticide and fertilizer occurs.

* * * * *